(12) United States Patent
Scholan

(10) Patent No.: US 10,960,547 B2
(45) Date of Patent: Mar. 30, 2021

(54) ROBOT ARM LOCATION

(71) Applicant: CMR SURGICAL LIMITED, Cambridge (GB)

(72) Inventor: Andrew Murray Scholan, Waltham Cross (GB)

(73) Assignee: CMR SURGICAL LIMITED, Cambridge (GB)

(*) Notice: Subject to any disclaimer, the term of this patent is extended or adjusted under 35 U.S.C. 154(b) by 310 days.

(21) Appl. No.: 16/060,439

(22) PCT Filed: Dec. 9, 2016

(86) PCT No.: PCT/GB2016/053886
§ 371 (c)(1),
(2) Date: Jun. 8, 2018

(87) PCT Pub. No.: WO2017/098261
PCT Pub. Date: Jun. 15, 2017

(65) Prior Publication Data
US 2018/0370036 A1  Dec. 27, 2018

(30) Foreign Application Priority Data

Dec. 10, 2015 (GB) .................................. 1521814
Jul. 5, 2016 (GB) .................................. 1611731

(51) Int. Cl.
B25J 9/00 (2006.01)
B25J 9/16 (2006.01)
(Continued)

(52) U.S. Cl.
CPC ............. *B25J 9/1692* (2013.01); *A61B 34/30* (2016.02); *A61B 34/35* (2016.02); *A61B 90/50* (2016.02);
(Continued)

(58) Field of Classification Search
CPC ...... B25J 9/1692; B25J 13/089; B25J 9/0009; B25J 9/1697; A61B 34/30; A61B 90/50;
(Continued)

(56) References Cited

U.S. PATENT DOCUMENTS 9,925,011 B2   3/2018  Gombert et al.
2006/0149418 A1* 7/2006  Anvari .................. A61G 13/10
                                                    700/245
(Continued)

FOREIGN PATENT DOCUMENTS

DE  102012110193 A1  4/2014
DE  102013012397 A1  1/2015
(Continued)

OTHER PUBLICATIONS

International Search Report from corresponding PCT/GB2016/053886 dated Feb. 13, 2017.
(Continued)

*Primary Examiner* — Ian Jen
(74) *Attorney, Agent, or Firm* — Lando & Anastasi, LLP

(57) ABSTRACT

A surgical robot arm (10) comprises a mounting portion (18). The mounting portion (18) comprises a reader (20) configured for reading location identifiers (26). The mounting portion (18) fits into a socket (22) comprising a location identifier (26). A signal output from the reader (20) allows determination of the location of the robot arm (10).

19 Claims, 6 Drawing Sheets

(51) Int. Cl.

| | | |
|---|---|---|
| *A61B 90/50* | (2016.01) | |
| *A61B 34/35* | (2016.01) | |
| *A61B 90/98* | (2016.01) | |
| *A61B 34/30* | (2016.01) | |
| *B25J 13/08* | (2006.01) | |
| *A61B 17/00* | (2006.01) | |
| *A61B 90/96* | (2016.01) | |

(52) U.S. Cl.
CPC ............ *A61B 90/98* (2016.02); *B25J 9/0009* (2013.01); *B25J 9/1697* (2013.01); *B25J 13/089* (2013.01); *A61B 90/96* (2016.02); *A61B 2017/00482* (2013.01)

(58) Field of Classification Search
CPC .................... A61B 34/35; A61B 90/98; A61B 2017/00482; A61B 90/96; A61B 90/90
See application file for complete search history.

(56) References Cited

U.S. PATENT DOCUMENTS

| | | |
|---|---|---|
| 2014/0118800 A1 | 5/2014 | Hwang |
| 2015/0175218 A1 | 6/2015 | Yoshioka et al. |

FOREIGN PATENT DOCUMENTS

| | | |
|---|---|---|
| DE | 102013111935 A1 | 4/2015 |
| DE | 102013220329 A1 | 4/2015 |
| DE | 102014203921 A1 | 9/2015 |
| JP | 2003181786 A | 7/2003 |
| WO | 2014118800 A1 | 8/2014 |
| WO | 2015142798 A1 | 9/2015 |
| WO | 2015142802 A1 | 9/2015 |
| WO | 2015142812 A1 | 9/2015 |
| WO | 2015175218 A1 | 11/2015 |
| WO | 2016048738 A1 | 3/2016 |

OTHER PUBLICATIONS

United Kingdom Search Report from corresponding United Kingdom Application No. GB1611731.9 dated Dec. 22, 2016.
European Examination Report from corresponding European Application No. 16815913.5 dated May 10, 2019.
English Translation of Japanese Notification of Reasons for Refusal from corresponding Japanese Patent Application No. 2018-529929 dated Oct. 27, 2020.

* cited by examiner

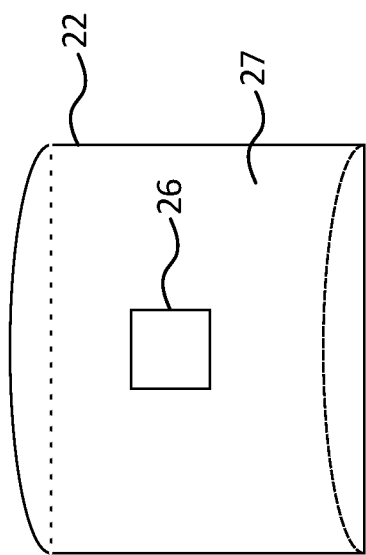
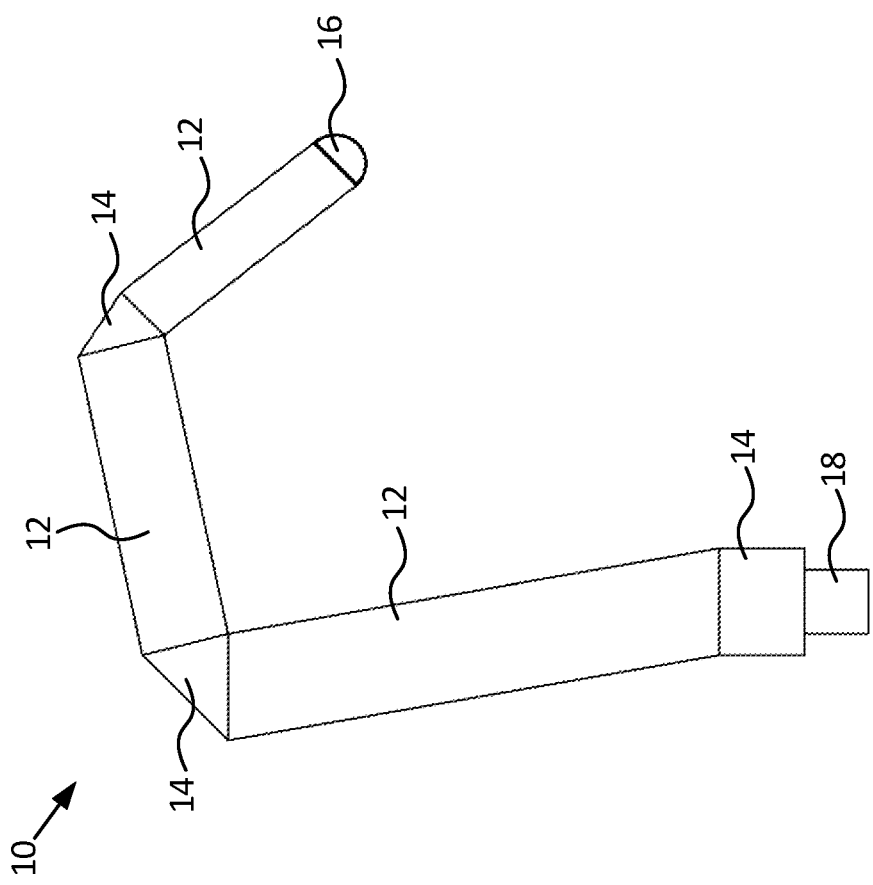

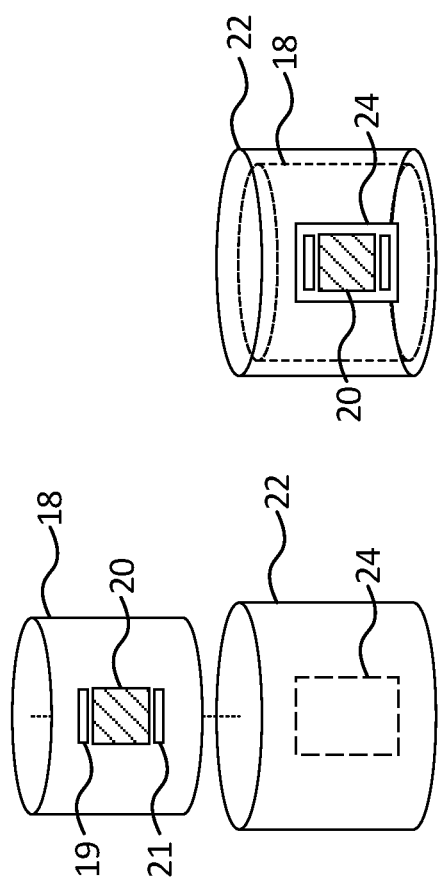
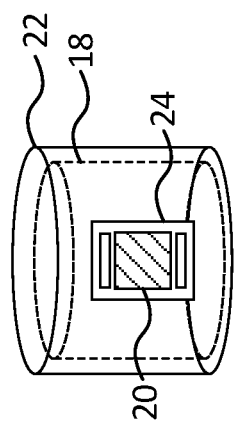
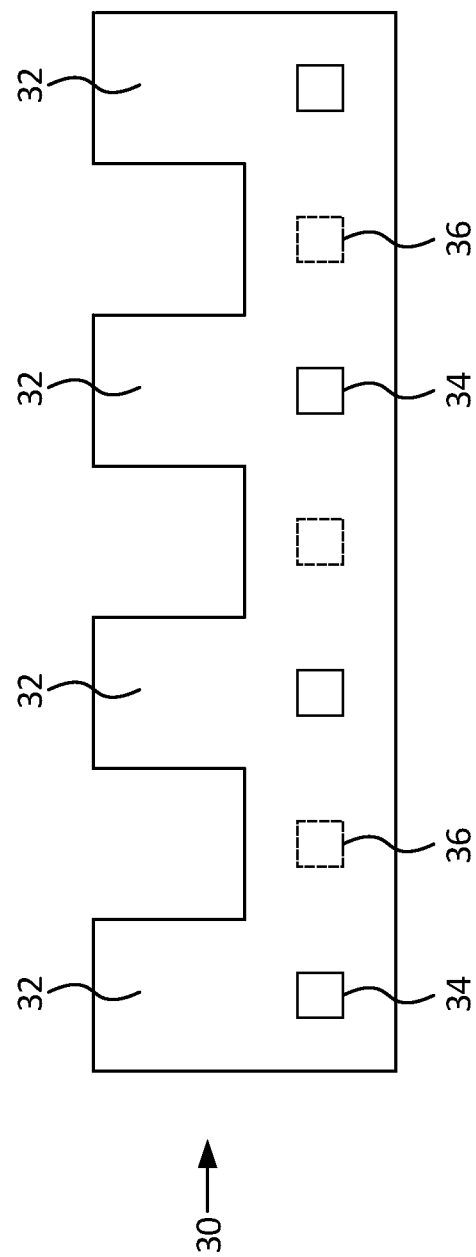

ROBOT ARM LOCATION

CROSS-REFERENCE TO RELATED APPLICATIONS

This application is a U.S. National Phase Application under 35 U.S.C. § 371 of International Application No. PCT/GB2016/053886, filed Dec. 9, 2016, which claims priority to United Kingdom Application No. 1521814.2, filed Dec. 10, 2015, and United Kingdom Application No. 1611731.9, filed Jul. 5, 2016, all of which are hereby incorporated by reference in their entireties for all purposes.

BACKGROUND

This invention relates to robot arms and to methods for locating robot arms.

Robotic systems that incorporate robot arms can be used in many situations where repeatability and/or precision of movement is desirable. One example of such robotic systems is a robotic surgical system.

It is highly desirable, especially in a robotic surgical system, that the position of a robot arm is known. This enables the motion of the arm to be accurately controlled, preventing damage to objects and/or people in the vicinity of the robot arm. This can be achieved in some systems by connecting several robot arms to a base unit. It is then possible to determine the relative positions of the arms to one another, using the base unit as a frame of reference.

The base unit is typically a common base unit, to which the several robot arms are connected.

In other systems, it is necessary to determine the location of each robot arm prior to use. This can be done by manoeuvring the arm so that the distal end of the arm touches a known point in the environment, such as on an operating table. Positional information could also be manually entered into the robotic system.

For separable robot arms, the need to carry out these separate calibration steps prior to use introduces delays into the system. These delays can be compounded where an arm is moved from one place to another, since the calibration step must then be carried out again when the arm is newly placed and before it can be used.

It may be difficult, or impossible, for an arm to be manoeuvred in a calibration step where the operating environment is crowded. In such cases, either the arm cannot be used, or it must be used without being able to accurately determine its location.

There is a need for an improved robot arm, and an improved method for locating a robot arm.

SUMMARY

According to one aspect of the present invention there is provided a robot arm comprising a mounting portion configured for mounting in a socket so as to support the robot arm, the mounting portion comprising a reader for reading a location identifier so as to determine the location of the robot arm.

The provision of a reader permits the determination of the location of the robot arm when mounted in the socket. The robot arm may be for use in a robotic surgical system.

Suitably the robot arm is a surgical robot arm.

Suitably the reader is configured to communicate with a processor for processing a signal received from the reader. Suitably the reader is configured to communicate with the processor at least in part by a wireless connection. This can minimise wiring needed and/or can increase flexibility of positioning of the reader on the robot arm. Suitably the reader is configured to send to the processor a signal in dependence on the reading by the reader of the location identifier. Suitably the processor is configured to receive the signal from the reader and to determine the location of the robot arm in dependence on the signal received from the reader.

The robot arm may comprise the processor. Suitably the processor is configured to send the result of the location determination to a central controller configured to control the robot arm.

The processor may be configured to send information, for example the signal received from the reader, to the central controller. The central controller may be configured to determine the location of the robot arm in dependence on the information received from the processor, for example in dependence on the signal received from the reader.

Suitably the processor is remote from the robot arm. Suitably a central controller configured to control the robot arm comprises the processor.

Suitably the reader is provided on a portion of the mounting portion which is arranged to be within the socket when the mounting portion is mounted in the socket.

The reader may be provided at an exterior location, for example on an exterior surface, of the mounting portion, to allow the reader to read location identifiers adjacent or near to the robot arm. The mounting portion may comprise a window, and the reader may be provided within the mounting portion such that it can read location identifiers through the window. This arrangement can provide the reader with some physical protection from knocks and/or environmental conditions.

Suitably the reader is configured to read the location identifier at least one of optically and magnetically. Suitably the window is at least one of optically and magnetically transparent, to permit optical and/or magnetic reading of the location identifier by the reader through the window. Suitably the window is a solid material. The reader may be a code reader, for example a QR code reader. The location identifier may be an optical code such as a QR code. Provision of a reader which can read an orientation-specific code such as a QR code can enable the reader to determine additional information, for example orientation information, as well as location information.

The window may comprise a hole in the mounting portion. The whole of the mounting portion may comprise the window. Suitably the mounting portion is transparent to permit the reading of the location identifier by the reader. In other words, the whole of the mounting portion may be transparent. The whole of the mounting portion, or a portion of the mounting portion, may act as the window.

The reader may be configured to read the location identifier electromagnetically, for example via at least one of radio waves, inductively and capacitively. Suitably the window is electromagnetically transparent, to permit electromagnetic reading of the location identifier by the reader through the window. The window is considered transparent if the reader can read the location identifier through the window.

Suitably the reader is configured to read a matrix bar code or a 2D bar code. Suitably the location identifier comprises a matrix bar code or a 2D bar code. The reader may be configured to read a magnetic code or pattern. Suitably the location identifier comprises a magnetic code or pattern. The reader may be configured to read one or more of a RFID identifier, an inductive identifier and a capacitive identifier.

The location identifier may comprise one or more of a RFID identifier, an inductive identifier and a capacitive identifier.

The robot arm may comprise a light for illuminating the location identifier. The provision of the light can permit the reader to read the location identifier even in low light conditions. Suitably the mounting portion comprises the light. The robot arm may comprise a light sensor for sensing the light level. The light may be arranged to turn on in dependence on the light level sensed by the light sensor. The robot arm may comprise a local power source for powering at least one of the reader, the light and the light sensor. The robot arm may comprise a power connection permitting the robot arm to be connected to an external source of power for powering at least one of the reader, the light and the light sensor.

According to another aspect of the present invention, there is provided a robotic system comprising the robot arm as defined above and a socket configured to receive at least a portion of the mounting portion of the robot arm. The robotic system may be a robotic surgical system.

According to another aspect of the present invention, there is provided a socket configured to receive at least a portion of the mounting portion of the robot arm.

The socket may comprise the location identifier. Suitably the location identifier is provided at an interior location, for example on an inside surface, of the socket. This arrangement allows the reader to easily read the location identifier when the mounting portion is mounted in the socket. This arrangement also restricts inadvertent reading of the location identifier by a reader of a robot arm not mounted in the socket.

The socket may be configured to receive the mounting portion of the robot arm in a plurality of orientations. Suitably the plurality of orientations are arranged rotationally about an axis of insertion of the mounting portion into the socket. The socket may comprise a plurality of location identifiers, each corresponding to a respective one of the plurality of orientations.

The socket is preferably configured so that the respective ones of the plurality of location identifiers are aligned with the reader when the mounting portion is mounted in the socket in the respective ones of the plurality of orientations.

Suitably the socket is movable between a first location and a second location so that a single socket can be used to mount the robot arm in the first and second locations. The socket may be movable between the first and second locations with the robot arm mounted in the socket. Suitably the socket comprises a first socket window through which one of a first location identifier at the first location and a second location identifier at the second location can be read by the reader. Suitably the first socket window is configured to be aligned with the reader when the mounting portion is mounted in the socket.

Suitably the socket comprises a plurality of socket windows through which the plurality of location identifiers can be read by the reader. Suitably the plurality of socket windows correspond to the plurality of location identifiers. In other words, the plurality of socket windows may correspond to the plurality of orientations.

Suitably the first socket window and/or at least one of the plurality of socket windows is at least one of optically and magnetically transparent, to permit optical and/or magnetic reading of the location identifier by the reader. Suitably the first socket window and/or at least one of the plurality of socket windows is a solid material.

Suitably the first socket window and/or at least one of the plurality of socket windows is electromagnetically transparent, to permit electromagnetic reading of the location identifier by the reader, for example via at least one of radio waves, inductively and capacitively.

The socket may be movable on or along a mounting apparatus, the mounting apparatus comprising a plurality of indexed mounting locations. The indexed mounting locations can include the first location and the second location. In other words, the mounting apparatus may provide for the socket to be located in discrete mounting locations on or along the mounting apparatus. Suitably each indexed mounting location is provided with a respective location identifier. The respective location identifiers may be provided at an exterior location, for example on an exterior surface, of the mounting apparatus adjacent the respective indexed mounting location.

Suitably the mounting apparatus is a crenellated rail. The socket may be configured to be locatable at positions along the crenellated rail adjacent at least some of the protrusions and/or recesses of the rail. The crenellated rail may comprise location identifiers at positions adjacent at least some of the protrusions and/or recesses of the rail. That is to say, the crenellated rail may comprise location identifiers at positions adjacent or near to the positions along the crenellated rail at which the socket is locatable.

Suitably the socket comprises a socket power connection for connecting to the power connection of the robot arm. Suitably the socket comprises a signal connection for connecting to the robot arm to transfer signals from the robot arm to a central controller configured to control the robot arm.

The robotic system may comprise the processor. The robotic system may comprise the central controller.

According to another aspect of the present invention, there is provided a method of determining the location of a robot arm, the robot arm comprising a mounting portion, the mounting portion comprising a reader, the method comprising mounting at least a portion of the mounting portion in a socket, reading a location identifier with the reader and in dependence on the reading of the location identifier with the reader, determining the location of the robot arm.

The method may comprise sending a signal from the reader to a processor and determining at the processor the location of the robot arm. The processor may be a remote processor.

The robot arm may comprise a light, and the method may comprise turning on the light to illuminate the location identifier, and reading the location identifier with the reader when the light is on.

The robot arm may comprise a light sensor, and the method may comprise sensing with the light sensor the light level, determining whether the light level is sufficient to illuminate the location identifier to be read by the reader, and if not, of turning the light on.

Any one or more feature of any aspect above may be combined with any one or more feature of any other aspect above. Any apparatus feature may be written as a method feature where possible, and vice versa. These have not been written out in full here merely for the sake of brevity.

BRIEF DESCRIPTION OF DRAWINGS

The present invention will now be described by way of example only with reference to the accompanying drawings. In the drawings:

FIG. 1 schematically shows a robot arm;

FIG. 2a schematically shows a mounting portion of a robot arm and a socket;

FIG. 2b schematically shows the mounting portion of FIG. 2a mounted in the socket of FIG. 2a;

FIG. 3 shows a partial section of a socket;

FIG. 4 shows a crenellated rail;

DETAILED DESCRIPTION

Figure 5:
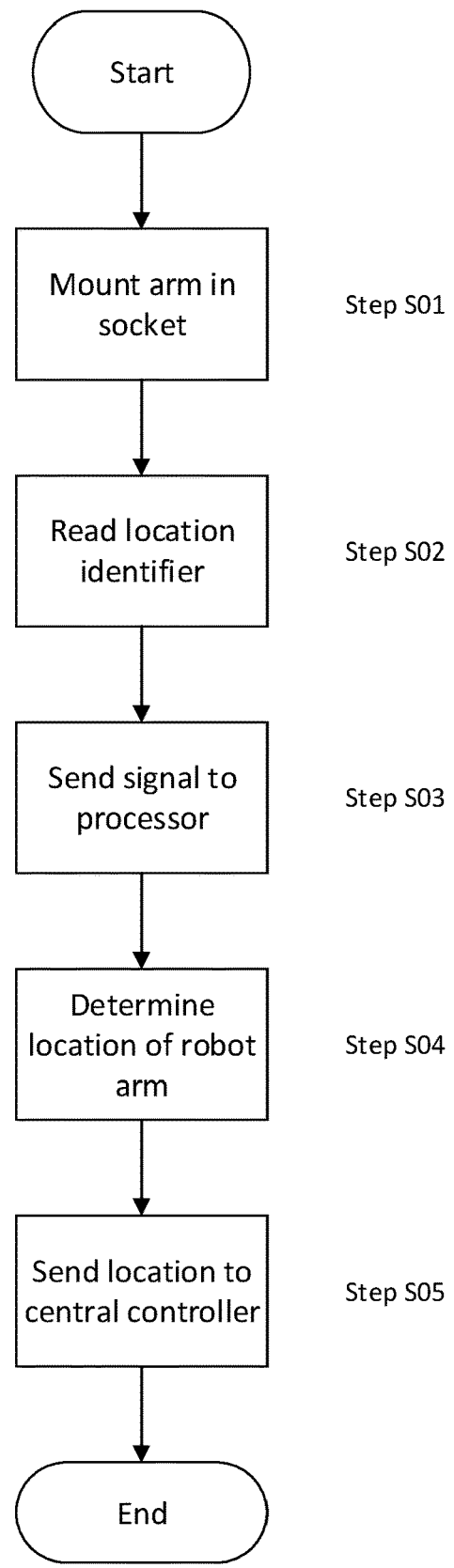
FIG. 5 shows a process of determining the location of a robot arm.

Robotic surgical systems permit precise control of surgical implements and the like by a surgeon through use of one or more robot arm. Typically the surgeon works at a remote workstation rather than directly at a surgical opening in a patient. The use of a robot arm permits use of various surgical tools which can be inserted through a smaller surgical opening than used in traditional surgery. The smaller surgical openings needed for surgery can improve patient recovery time following surgery.

A robot arm 10 for use in robotic surgical systems is shown schematically in FIG. 1. The robot arm 10 comprises a plurality of arm segments 12 coupled to one another by a plurality of joints 14. A tool portion 16 for carrying a surgical tool (not shown) is provided towards the distal end of the robot arm 10, and a mounting portion 18 is provided towards the proximal end of the robot arm 10. In some examples the joints 14 are one or other of revolute joints and prismatic joints. In some examples the joints are some combination of revolute, prismatic and/or other forms of joint. The joints 14 permit the tool portion to move relative to the mounting portion 18 such that the robot arm 10 can be controlled to position a tool carried by the tool portion 16 in a desired position and orientation.

In some examples the surgical tool carried by the tool portion 16 of the robot arm 10 can be changed during a surgical procedure. In some examples it is desirable to leave the surgical tool in place on the robot arm 10, and to change the robot arm 10 instead. Thus, it is desirable that the robot arm 10 can easily be mounted to and demounted from the robotic surgical system.

In some examples, whether or not the surgical tool carried by the tool portion 16 of the robot arm 10 is to be changed, it is desirable to change the position of the robot arm 10. This might be the case when, for example, the robot arm 10 is to be used on a different surgical site in the same procedure, or in the same surgical site but in a different configuration. In these examples as well, it is desirable that the robot arm 10 can easily be mounted to and demounted from the robotic surgical system.

In some examples, a robotic surgical system comprises a central controller which receives inputs, for example from a surgeon workstation, and outputs control signals to a robot arm 10 to effect desired movement of the robot arm 10. For the central controller to accurately control the movement of the robot arm 10 it is desirable for the location of the robot arm 10 to be known. Therefore, before the robot arm 10 is used in the surgical procedure, its location is input into the system.

Where, as in some examples mentioned, robot arms are changed either at the start of or during a surgical procedure, it is desirable for the location of each robot arm to be input to the system with minimal delay and/or maximal accuracy.

This approach enables efficient use of the system in a surgical procedure. If long delays were introduced when moving robot arms, this would prolong the surgical procedure, which is undesirable.

The robot arm 10 is mountable in a socket 22. This is shown schematically in FIG. 2. The robot arm 10 is mountable in the socket 22 by the mounting portion 18. FIG. 2a shows the mounting portion 18 (the remainder of the robot arm 10 is omitted here for clarity) and the socket 22 separate from one another, and FIG. 2b shows the mounting portion 18 within the socket 22. The socket 22, in some examples, forms part of the robotic surgical system. The socket 22 is configured to receive at least a portion of the mounting portion 18 of the robot arm 10 so as to hold the robot arm 10 in place. The mounting portion 18 is, in some examples, configured to cooperate with the socket 22. In some examples the mounting portion 18 is configured to be seated substantially within the socket 22. This can provide a more firm hold of the robot arm 10 by the socket 22.

In one example the mounting portion 18 is cylindrical and is configured to lock into place in the socket 22. The mounting portion 18, in one example, comprises a projecting lug which is receivable into a recess or channel in the socket 22. The lug is receivable into a first channel portion on insertion of the mounting portion 18 into the socket 22 in a mounting direction. The mounting portion 18 is rotatable about the axis of insertion (along the mounting direction) to enable the lug to pass into a second channel portion which communicates with and is configured at an angle to the first channel portion. The second channel portion is configured to retain the lug so that the mounting portion 18 is retained in the socket 22. In one configuration the mounting portion 18 is not removable from the socket 22 without being rotated again about the axis of insertion so as to cause the lug to move into the first channel portion.

Two or more lugs, and two or more recesses or channels could also be used. Where a plurality of lugs and recesses are used, it is preferable for the lugs to be spaced about the circumference of the mounting portion and for the recesses to be correspondingly spaced about the circumference of the socket. Equal spacing of the lugs and recesses can assist in stability of the retention of the mounting portion in the socket.

Similarly, one or more lugs may be provided on the socket, and a corresponding one or more recesses or channels may be provided on the mounting portion.

Other mechanisms for locking the mounting portion in place in the socket will be apparent to the skilled person.

An approach to easily and/or accurately determine the location at which a robot arm 10 is located is to use location identifiers. A location identifier can be provided at a particular location so as to identify that location. The location identifier may uniquely identify the location. The location identifier can be read by a reader. The reading by the reader of the location identifier indicates that the reader is at the particular location.

In one example the reader is configured to produce a signal on reading a location identifier. The signal is sent to a processor. The processor is configured to determine the location in dependence on the signal. In one example the processor is configured to use the signal to reference a look-up table, from which the location can be determined. In another example the location identifier may directly identify the location, so that the processor is enabled to determine the location on the basis of the signal. For example, the signal may provide details of the location at which the location identifier giving rise to that signal is located.

The mounting portion 18 comprises a reader 20 for reading location identifiers. In some examples, the socket 22 comprises a location identifier 26 (see FIG. 3). In some examples the location identifier is provided at an interior location, for example on an inside surface 27, of the socket. The mounting portion 18 and the socket 22 are configured so that, on mounting the mounting portion 18 in the socket 22, the reader 20 is able to read the location identifier 26.

In some examples the location identifier 26 is configured to be read optically. In some examples the location identifier 26 is additionally or alternatively configured to be read magnetically. The reader 20 is configured to read location identifiers at least one of optically and magnetically. For example, the location identifier 26 can be an optical code such as a QR code, and the reader 20 can be an optical code reader such as a QR code reader. In some examples the reader 20 is a camera.

In some examples the location identifier 26 is configured to be read electromagnetically, for example via radio waves, inductively and/or capacitively. In these examples, the reader 20 is configured to read the location identifier electromagnetically, for example via at least one of radio waves, inductively and capacitively.

The reader 20 is, in some examples, provided on an exterior surface of the mounting portion 18. In other examples, the reader 20 is provided in the interior of the mounting portion 18 and the mounting portion 18 is configured so that the reader 20 is able to read location identifiers in the vicinity of the mounting portion 18. In some examples the mounting portion 18 comprises a window (not shown) through which the reader can read location identifiers. The provision of the window can provide some environmental protection to the reader 20. In some examples, the window is solid, for example glass or plastic such as clear plastic. The window is configured to be at least partially transparent such that the reader 20 is able to read location identifiers through the window. In other words, where the location identifier is read optically, the window is at least partially optically transparent so that the reader 20 can optically read the location identifier 26 through the window. Where the location identifier is read magnetically, the window is at least partially magnetically transparent so that the reader 20 can magnetically read the location identifier 26 through the window.

Where the location identifier 26 is configured to be read electromagnetically, the window is at least partially electromagnetically transparent.

In some examples, such as where the socket 22 is movable, the location identifier 26 is not provided on the socket 22 itself, but is instead provided adjacent or near to the socket 22 location. In some examples, where the socket 22 is movable, a plurality of location identifiers are provided, each adjacent or near to one of the socket 22 locations.

In some examples, the socket 22 comprises a first socket window 24 (the first socket window 24 is shown in dashed lines in FIG. 2a to indicate that it is optional). The first socket window is provided such that the location identifier 26 can be read by the reader 20 through the first socket window 24. In other words, when a robot arm 10 is mounted in the socket 22, the reader 20 can read the location identifier 26 through the first socket window. Reference is made to FIG. 2b, which shows the mounting portion 18 mounted in the socket 22; the reader 20 is aligned with the first socket window 24, and is able to read location identifiers through the first socket window 24.

In some examples, the first socket window 24 is at least partially optically and/or magnetically transparent. This permits the reader 20 to read location identifiers optically and/or magnetically through the first socket window 24. In some examples the first socket window 24 is solid. In some examples the first socket window is glass or plastic, such as clear plastic. This can provide some environmental protection to the reader 20 and/or the mounting portion 18 when mounted in the socket 22. It can also restrict entry of environmental material, such as dust and/or detritus, into the socket 22 interior.

In some examples, the first socket window 24 is at least partially electromagnetically transparent. This permits the reader 20 to read location identifiers electromagnetically through the first socket window 24.

Where the location identifier 26 is provided on an exterior surface, this can include attaching the location identifier 26 to the exterior surface by adhesive, such as sticking an optical code and/or a magnetic code onto the surface. It can also include etching a pattern such as an optical code into the surface.

Providing the location identifier 26 on an exterior surface can also include magnetising the surface in a pattern, or attaching one or more of a RFID identifier, an inductive identifier and a capacitive identifier to the surface.

In some examples, the robotic system comprising the mounting portion 18 and the socket 22 has a plurality of configurations. The robotic system is in some examples configured so that the mounting portion 18 is mountable in the socket 22 in a plurality of orientations. For example, the plurality of orientations can be arranged rotationally about an axis of insertion of the mounting portion 18 into the socket 22. In one example, a first orientation is arranged at a 90 degree rotational offset from a second orientation. In this example, the robotic system is configured so that the socket 22 permits mounting of the robot arm 10 in either of the first or second orientation. This permits additional flexibility in the use of the robot arm 10. In this example, each of the first and second orientations has associated therewith a respective location identifier 26. These are provided such that on mounting the robot arm 10 in the first orientation, the reader 20 is enabled to read the location identifier associated with the first orientation; on mounting the robot arm 10 in the second orientation, the reader 20 is enabled to read the location identifier associated with the second orientation. In this way, the location and orientation of the robot arm 10 can be determined.

The location identifiers are, in some examples, associated with the first and second orientations by being provided on an interior, such as on an interior surface, of the socket 22. The location identifiers are provided spaced from one another, by 90 degrees around the socket 22 in this example. This may be the case where the socket 22 is not movable.

The location identifiers are, in some examples, associated with the first and second orientations by being provided adjacent or near to the socket 22. In this example the socket 22 comprises the first socket window and a second socket window, spaced from the first socket window by a 90 degree rotation about the socket 22 axis. One of the location identifiers is provided adjacent or near to the first socket window and the other of the location identifiers is provided adjacent or near to the second socket window. In this way, the reader 20 can read one of the location identifiers through the first socket window when the robot arm 10 is mounted in the socket 22 in the first orientation. The reader 20 can read the other of the location identifiers through the second socket window when the robot arm 10 is mounted in the socket 22 in the second orientation.

In more general terms, the plurality of location identifiers associated with the plurality of orientations (and the plurality of socket windows, where present) are spaced from one another about the axis of the socket. They need not be equally spaced, depending on the desired configurations.

In some examples, the reader 20 is provided on the mounting portion 18 such that it aligns with the location identifier, or a respective one of the location identifiers, on insertion of the mounting portion 18 into the socket 22. In some examples the location identifier 26, or at least one of the location identifiers, is configured so that it can only be read by the reader 20 when the mounting portion 18 is mounted in the socket 22. In some examples, the location identifier 26, or at least one of the location identifiers, is configured so that it can only be read by a reader 20 within a predetermined proximity of the respective location identifier 26. Thus, where the location identifier 26 is configured to be read magnetically, the reader 20 needs to be close enough to the location identifier 26 before it can read it. This reduces the likelihood that a reader 20 inadvertently reads the location identifier 26 when not mounted in the socket 22.

Where the location identifier 26 is configured to be read optically, it is, in some examples, provided in a position where it cannot easily be read by a reader 20 that is not mounted in the socket 22. The location identifier 26 is, in some examples, provided such that there is no direct line of sight to the location identifier from the reader 20 unless the reader 20 is mounted in the socket 22. This reduces the likelihood that a reader 20 inadvertently reads the location identifier 26 when not mounted in the socket 22.

In some examples the socket 22 is movable between a first location and a second location. More than two locations are also possible. In these examples, the socket 22 comprises at least one socket window 24, and each of the locations has associated therewith a respective location identifier 26. The location identifier 26 is, in some examples, provided adjacent or near to the respective location such that it can be read through the socket window 24 by the reader 20 of a robot arm 10 mounted in the socket 22.

In some examples the socket 22 is movable between the first and second locations along or on a mounting apparatus. The mounting apparatus is configured to support the socket 22 at each of the first and second locations such that the robot arm 10 can be held by the socket 22 at each of those locations. The locations are discretely provided along the mounting apparatus. Each location can be considered as a separate mounting location. Each location has associated therewith a respective location identifier. In some examples, the respective location identifiers are provided on the mounting apparatus so as to be read by the reader 20 of a robot arm 10 mounted by the socket 22 at that respective location. In some examples, the location identifiers are provided on the exterior surface of the mounting apparatus adjacent or near to the respective mounting location.

One example of a mounting apparatus is a crenellated rail 30, as shown schematically in FIG. 4. Four crenellations 32 are shown, but greater or fewer crenellations are possible. In the illustrated example the socket 22 is configured to be locatable at both the projections 32 and recesses along the crenellated rail. In other examples the socket 22 and/or the crenellated rail 30 may be configured such that the socket 22 is locatable at either the projections 32 or the recesses, or at least some of the projections 32 and recesses.

For each of the possible locations of the socket 22 along the crenellated rail 30, a location identifier is provided. Referring to FIG. 4, a plurality of location identifiers 34 are aligned with the socket 22 when the socket 22 is located at the respective projection 32, and a plurality of location identifiers 36 are aligned with the socket 22 when the socket 22 is located at the respective recess.

The provision of the crenellated rail 30 permits the robot arm 10, together with the socket 22, to be moved to a convenient location along the crenellated rail 30. The operator can move the arm 10 to the position that, for example, provides the most appropriate access to a surgical site (in the context of a robotic surgical system). Once located, the reader 20 of the robot arm 10 will read the location identifier 26 at that location. This permits the location of the robot arm 10 to be determined automatically without further action required by the operator or by requiring the arm 10 to undertake any calibration actions.

The crenellated rail 30 need not be a straight rail. It can adopt any desired shape as long as the available positions and/or orientations along the rail 30 are known. The crenellated rail 30 can be provided alongside the bed. Alternatively, the crenellated rail 30 can be provided as part of the bed, for example as a bed side rail. In another alternative, the crenellated rail 30 can be mounted to another part of the operating room, for example the ceiling or a wall. When ceiling- or wall-mounted, the robot arm may depend from the crenellated rail 30 towards a surgical site. In other words, the robot arm may extend generally downwards from the crenellated rail 30 towards the surgical site.

Any combination of shape and location of crenellated rails may be provided.

This approach can increase the flexibility with which robot arms 10 can be located, and can decrease the time required before the robot arms 10 can be used.

In some examples, either where the location identifier 26 is provided within the socket 22 or adjacent or near to the socket 22, poor lighting conditions may exist which can make it difficult to accurately read the location identifier 26 optically. The robot arm 10 can, in some examples, comprise a light 19 for illuminating the location identifier 26 such that it can more easily and/or accurately be read by the reader 20. In some examples, the mounting portion 18 comprises the light 19. This arrangement allows the light 19 to be provided adjacent or near to the reader 20. A relatively lower power light may therefore provide an acceptable level of illumination for the reader 20 to read the location identifier 26. This can save power and/or reduce potentially distracting light that might otherwise be emitted.

Light levels in the environment of the reader 20 and location identifier 26 may change. In some examples, the robot arm 10 comprises a light sensor 21 for sensing the light level. In some examples, the mounting portion 18 comprises the light sensor 21. Advantageously the light sensor 21 is provided in the vicinity of the location identifier 26 so that it can sense the light level at the location identifier. The light 19 is configured in some examples to turn on when the light level sensed by the light sensor 21 is below a predetermined threshold.

In some examples a processor (not shown) is provided for processing signals received from at least one of the reader 20 and the light sensor 21. In some examples the processor determines whether or not to turn the light 19 on in dependence on the signal received from the light sensor 21. In some examples, the processor determines the location of the robot arm 10 in dependence on the signal received from the reader 20.

In some examples the robotic system comprises the processor. In some examples the robot arm 10 comprises the processor. In some examples the processor is remote from the robot arm 10.

In some examples the socket 22 and the mounting portion 18 comprise complementary attachments for electrically connecting the socket 22 and the mounting portion 18 together. The attachments (not shown) permit power and/or signals to be transferred between the socket 22 (and hence the robotic surgical system) and the robot arm 10.

In some examples the mounting portion 18 of the robot arm 10 comprises a mounting sensor configured to sense when the mounting portion 18 is mounted in the socket 22. The reader 20 is in some examples configured to read the location identifier 26 in dependence on the sensing by the mounting sensor of when the mounting portion 18 is mounted in the socket 22. In this way, the reader reads the location identifier when it is determined that the robot arm 10 has been mounted in the socket 22.

In other examples, the socket 22 comprises at least one of the light 19, the light sensor 21 and the mounting sensor.

In some examples, the robot arm 10 and the robotic surgical system comprise wireless transceivers (or separate wireless transmitters and receivers) for transferring signals such as control signals and/or signals from the reader 20 and the light sensor 21.

Wireless transceivers (or separate wireless transmitters and receivers) can also be used to transfer signals from the mounting sensor. Additionally or alternatively, wired transceivers (or transmitters and receivers) can be used for transferring any signal.

With reference to FIG. 5, a method of determining the location of a robot arm 10 will now be described. Initially, the robot arm 10 is mounted in the socket 22 (step S01). The reader 20 then reads the location identifier 26 (step S02); as mentioned above, this can be in response to the sensing by a mounting sensor that the robot arm 10 has been mounted in the socket 22. At step S03 a signal is sent to the processor from the reader 20. In response to receiving the signal from the reader 20, which signal indicates the location identifier 26 read by the reader 20, the processor determines the location of the robot arm 10 (step S04).

Where the location identifier 26 is a code (either optical and/or magnetic) the location can be determined by decoding the code, for example by using a look-up table for a list of known locations.

As mentioned above, the location identifier 26 might comprise at least one of a RFID identifier, an inductive identifier and a capacitive identifier. Thus the code may additionally or alternatively be at least one of a RFID code, an inductive code and a capacitive code.

In some examples the code can identify a location within the look-up table at which the relevant position and/or orientation information is stored. In other examples the code can contain the position and/or orientation information. The orientation of the location identifier 26, for example the orientation of the code, can indicate the orientation of the socket 22.

In some examples, the method includes sending the determined location to the central controller (step S05) which can effect control of the robot arm 10 in dependence on the determined location.

Figure 6:
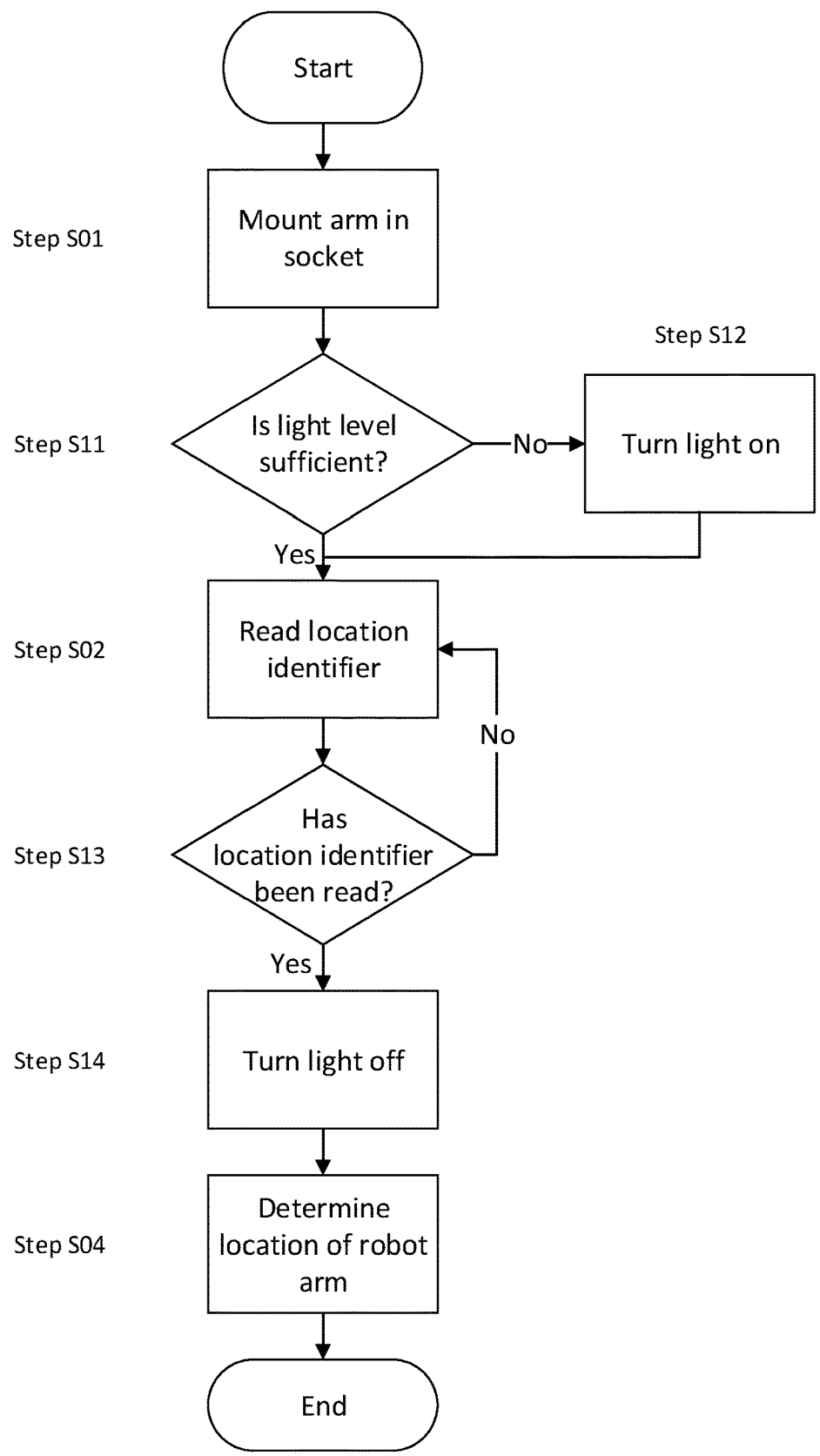
FIG. 6 shows another process of determining the location of a robot arm.

Referring now to FIG. 6, in one example, the method includes the following steps. In step S01, the robot arm 10 is mounted in the socket 22. The light sensor 21 then senses whether the light level is above a predetermined threshold at step S11; this can be in response to the sensing by a mounting sensor that the robot arm 10 has been mounted in the socket 22. If the light level is below the predetermined threshold, then at step S12 the light 19 is turned on, and the reader 20 reads the location identifier 26 (step S02). If the light level is at or above the predetermined threshold, then the method proceeds directly to step S02, i.e. the reader 20 reads the location identifier 26.

At step S13 a determination is made as to whether the reader 20 has read the location identifier 26. In one example, a determination that the location identifier has been read is made in dependence on the outputting of a signal from the reader 20 to the processor. Once it is determined that the location identifier 26 has been read, the light is turned off (step S14; this step is omitted where the light is not turned on). The location of the robot arm 10 is then determined as before (step S04).

Further, the robot arm can be configured to switch on the light 19 in response to determining that the robot arm is mounted in the socket 22. This may be irrespective of the light level sensed by the light sensor 21. The light 19 can be switched on in response to a signal from the mounting sensor. The light 19 can be switched on in response to an instruction from the processor. For example, the processor may be configured to determine when the robot arm is mounted to the socket 22, such as by receiving a signal from the mounting sensor, and in response to that determination to send an instruction to cause the light 19 to turn on.

The robot arm can be configured to switch off the light 19 in response to determining that (i) the identifier, such as the code, has been successfully read by the reader 20, (ii) a predetermined time has elapsed, such as a predetermined time after mounting the mounting portion into the socket, or a predetermined time after switching on the light, and/or (iii) an instruction has been received to switch off the light, for example an instruction from the processor.

Figure 7:
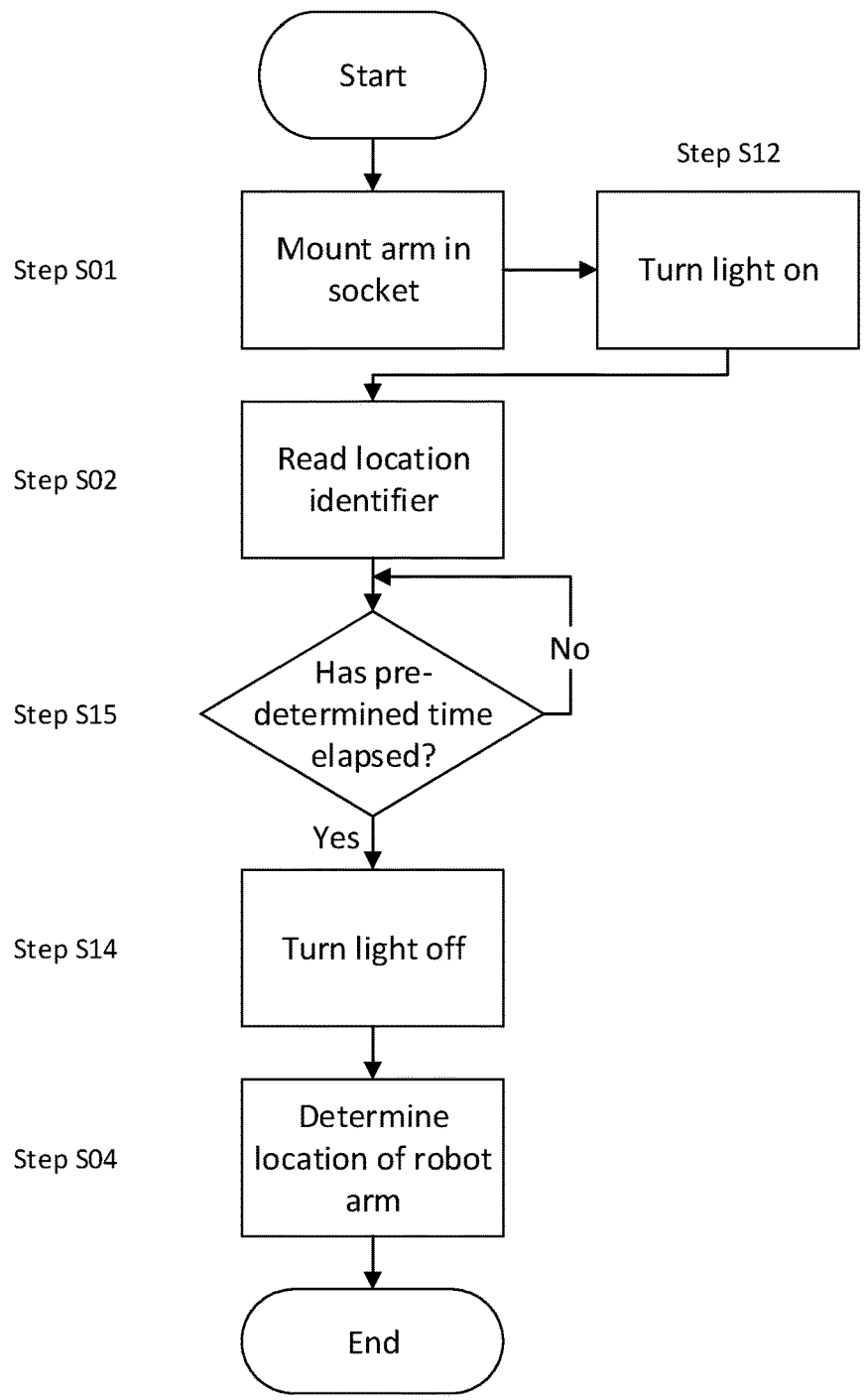
FIG. 7 shows another process of determining the location of a robot arm.

Referring to FIG. 7, at step S01, the robot arm 10 is mounted in the socket 22. In response to determining that the robot arm is mounted in the socket, the light is switched on at step S12. This determination can be made as described above. The reader 20 reads the location identifier 26 (step S02). The processor determines at step S15 whether the predetermined time period has elapsed. The predetermined time period can be measured by a clock local to the processor or spaced from and in connection with the processor. The clock is arranged to start running when the mounting portion is mounted in the socket, or when the light is switched on. Alternatively, a pre-running clock signal can be used as a start time. The processor is arranged to determine that the predetermined time has elapsed when the clock reaches the predetermined time period or when the difference between a current clock signal and the start time equals or exceeds the predetermined time period.

In some implementations the predetermined time period is adjustable, for example by a user. For example, the predetermined time period is approximately 5 seconds. In another example the predetermined time period is approximately 2 seconds. Alternatively the predetermined time period is approximately 1 second. The predetermined time period can be chosen to be the same or slightly greater (for example 1.5 times, or 2 times) a measured time or an average measured time taken for the reader 20 to read the location identifier 26.

When it is determined, for example by the processor, that the predetermined time period has elapsed (step S15) the light is switched off at step S14. Step S04 is shown as occurring subsequently, but it will be understood that the location of the robot arm can be determined at any time after the location identifier 26 has been read by the reader 20 (step S02). This is the case for this implementation as well as that discussed with reference to FIG. 6 above and FIG. 8 below.

In another implementation, which will now be discussed with reference to FIG. 8, the light 19 can be switched off in response to an instruction. The initial method steps can be some or all of the steps as in the process illustrated in FIG. 6 (i.e. steps S01, S11, S12, S02 and/or S13) and/or in FIG. 7 (i.e. steps S01, S12, S02 and/or S15) or some combination of some or all of these steps.

When the light is turned on, whether it was turned on in response to an instruction to do so, in response to detected light levels, and/or in response to detecting that the robot arm has been mounted in the socket, the light 19 can be turned off in dependence on an instruction (step S16). The instruction can be received from the processor. The instruction can be issued by the processor automatically or in response to a user interaction.

Following step S16, the light is switched off at step S14 and the location of the robot arm is determined at step S04. As mentioned above, step S04 can be carried out earlier in some implementations. The process need not wait for the light to be turned off before the location determination is made. Proceeding with step S04 as soon as the location identifier 26 has been read by the reader 20 can reduce the time taken for the location of the robot arm to be determined.

Figure 8:
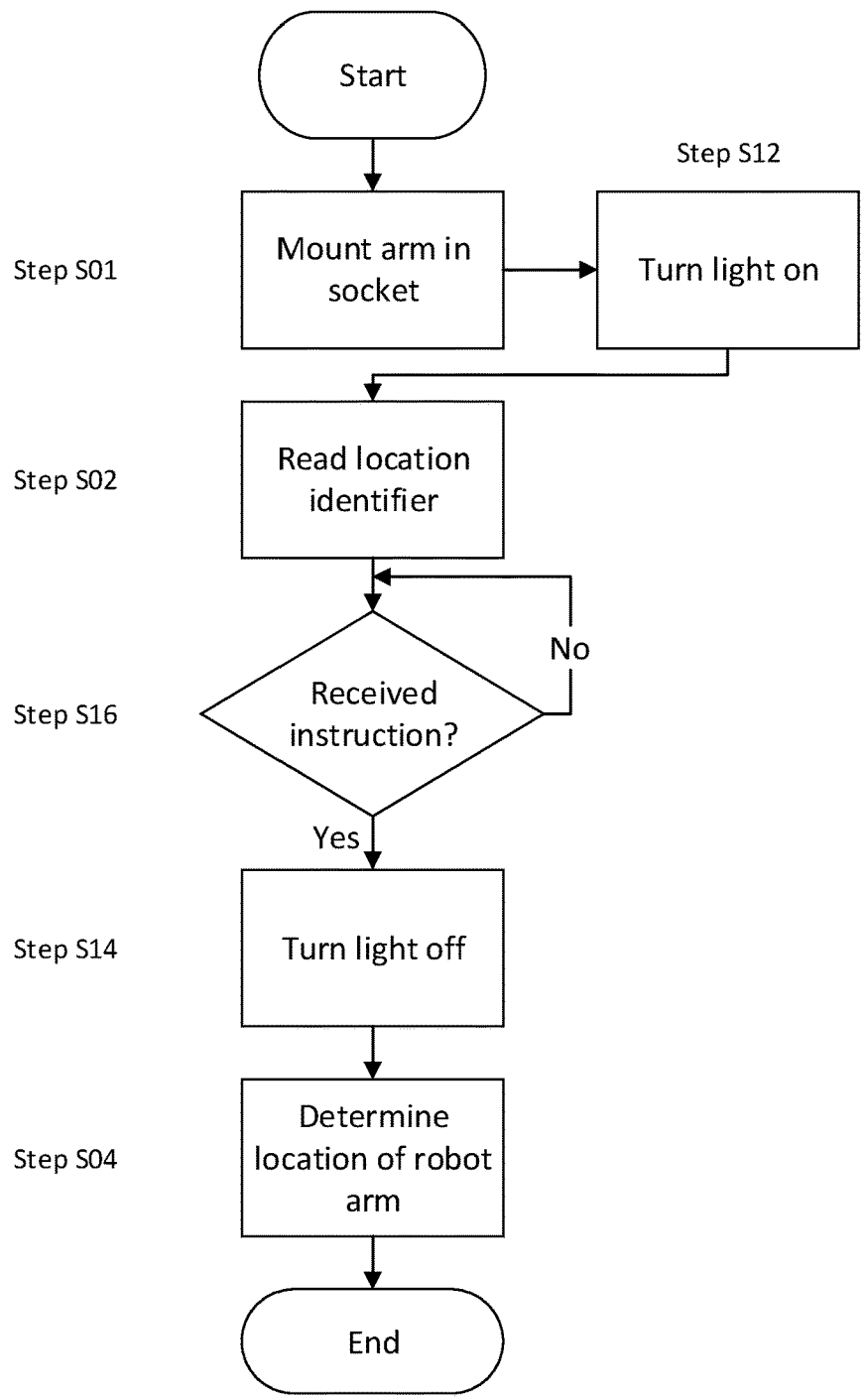
FIG. 8 shows another process of determining the location of a robot arm.

The above description, referring to FIGS. 6 to 8, mentions turning a light on and off. This is useful where the location identifier is to be read optically. The light need not be provided. In examples where the location identifier is not to be read optically, the light can be omitted. Alternatively or additionally to the light, there can be provided a different source of energy which can enable the location identifier to be read. For example, where the location identifier comprises a RFID identifier, the source of energy can be a source of RF energy to energise a passive RFID identifier. Other sources of energy can be chosen to match the other types of location identifier discussed above. The source of energy is suitably a source of electromagnetic energy.

In some examples, combinations of these method steps are possible.

Whilst the robot arm has been described above in the context of a surgical robot arm, the principles herein are applicable more broadly than this. The principles may also apply to industrial robots, or other types of robotic systems in which robot arms are used such as a configurable robot manipulator.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robot arm comprising a mounting portion configured for mounting in a socket so as to support the robot arm, the mounting portion comprising a reader for reading a location identifier so as to determine the location of the robot arm,
wherein the reader is provided on a portion of the mounting portion which is arranged to be within the socket when the mounting portion is mounted in the socket, and
wherein the reader is configured to communicate with a processor for processing a signal received from the reader, the reader being configured to send to the processor a signal in dependence on the reading by the reader of the location identifier.

2. A surgical robot arm as claimed claim 1, wherein the robot arm comprises the processor, and the processor is configured to receive the signal from the reader and to determine the location of the robot arm in dependence on the signal received from the reader.

3. A surgical robot arm as claimed in claim 2, wherein the processor is configured to send the result of the location determination to a central controller configured to control the robot arm.

4. A surgical robot arm as claimed in claim 1, wherein the reader is at least one of:
configured to read the location identifier electromagnetically; and
a 2D code reader.

5. A surgical robot arm as claimed in claim 1, wherein the robot arm comprises one or more of:
a light for illuminating the location identifier; and
a light sensor for sensing the light level.

6. A surgical robotic system comprising the robot arm as claimed in claim 1 and a socket configured to receive at least a portion of the mounting portion of the robot arm.

7. A surgical robotic system as claimed in claim 6, wherein the socket comprises the location identifier.

8. A surgical robotic system as claimed in claim 6, wherein the socket is configured to receive the mounting portion of the robot arm in a plurality of orientations.

9. A surgical robotic system as claimed in claim 6, wherein the socket is movable between a first location and a second location so that a single socket can be used to mount the robot arm in the first and second locations.

10. A surgical robotic system as claimed in claim 9, wherein the socket is movable between the first and second locations with the robot arm mounted in the socket.

11. A surgical robotic system as claimed in claim 9, wherein the socket comprises a first socket window through which one of a first location identifier at the first location and a second location identifier at the second location can be read by the reader.

12. A surgical robotic system as claimed in claim 11, wherein the first socket window is configured to be aligned with the reader when the mounting portion is mounted in the socket.

13. A surgical robotic system as claimed in claim 9, wherein the socket comprises a plurality of socket windows through which the plurality of location identifiers can be read by the reader.

14. A surgical robotic system as claimed in claim 11, wherein the first socket window and/or at least one of the plurality of socket windows is at least one of optically and electromagnetically transparent, to permit optical and/or electromagnetic reading of the location identifier by the reader.

15. A surgical robotic system as claimed in claim 9, wherein the socket is movable on or along a mounting apparatus, the mounting apparatus comprising a plurality of indexed mounting locations.

16. A surgical robotic system as claimed in claim 15, wherein each indexed mounting location is provided with a respective location identifier.

17. A surgical robotic system as claimed in claim 15, wherein the mounting apparatus is a crenellated rail.

18. A method of determining the location of a surgical robot arm, the robot arm comprising a mounting portion configured for mounting in a socket so as to support the robot arm, the mounting portion comprising a reader provided on a portion of the mounting portion which is arranged to be within the socket when the mounting portion is mounted in the socket, the reader configured to communicate with a processor for processing a signal received from the reader, the method comprising:
- mounting at least a portion of the mounting portion in the socket,
- reading a location identifier with the reader,
- sending, with the reader, a signal to the processor in dependence on the reading by the reader of the location identified, and
- in dependence on the reading of the location identifier with the reader, determining the location of the robot arm.

19. A method as claimed in claim 18, wherein the robot arm comprises a light sensor, and the method comprises sensing with the light sensor the light level, determining whether the light level is sufficient to illuminate the location identifier to be read by the reader, and if not, of outputting a signal to turn a light on.

* * * * *